(12) United States Patent
Yang et al.

(10) Patent No.: US 11,414,638 B2
(45) Date of Patent: Aug. 16, 2022

(54) PORTABLE BIOREACTOR

(71) Applicant: GENEREACH BIOTECHNOLOGY CORPORATION, Taichung (TW)

(72) Inventors: Wen-Shan Yang, Taichung (TW); Ching-Ko Lin, Taichung (TW); Fu-Chun Li, Taichung (TW); Pin-Hsing Chou, Taichung (TW); Yun-Lung Tsai, Taichung (TW); Pei-Yu Lee, Taichung (TW); Hsiao-Fen Chang, Taichung (TW)

(73) Assignee: GENEREACH BIOTECHNOLOGY CORPORATION, Taichung (TW)

( * ) Notice: Subject to any disclaimer, the term of this patent is extended or adjusted under 35 U.S.C. 154(b) by 413 days.

(21) Appl. No.: 16/803,414

(22) Filed: Feb. 27, 2020

(65) Prior Publication Data
US 2021/0147780 A1    May 20, 2021

(30) Foreign Application Priority Data

Nov. 18, 2019  (TW) .................................. 108141778

(51) Int. Cl.
*C12M 1/00*    (2006.01)
*C12M 3/00*    (2006.01)

(52) U.S. Cl.
CPC ............ *C12M 23/52* (2013.01); *C12M 23/40* (2013.01); *C12M 23/48* (2013.01)

(58) Field of Classification Search
CPC ...... C12M 23/40; C12M 23/48; C12M 23/52; C12M 23/54
See application file for complete search history.

(56) References Cited

U.S. PATENT DOCUMENTS

| 5,158,895 | A | * | 10/1992 | Ashihara | .......... | G01N 33/54326 435/7.1 |
| 11,221,331 | B2 | * | 1/2022 | Van Cleve | ............ | B01L 3/5082 |
| 2013/0132006 | A1 | * | 5/2013 | Gwynn | .................. | B01L 3/021 702/55 |
| 2016/0245834 | A1 | * | 8/2016 | Liu | ........................ | C12M 33/06 |

* cited by examiner

*Primary Examiner* — Lydia Edwards
(74) *Attorney, Agent, or Firm* — Birch, Stewart, Kolasch & Birch, LLP

(57) ABSTRACT

A portable bioreactor is provided for driving displacement of at least one stirring sleeve relative to at least one tube cassette in a first direction and includes a machine frame unit and a first elevator. The first elevator includes a first linear movement module, a first transmission module, and a first turning module. The first linear movement module includes a first slider which is slidable on the first guide rail in the first direction between a first top position and a first bottom position. The first turning module is coupled to the first slider through the first transmission module so as to permit turning of the first turning module to be translated by the first transmission module into linear sliding movement of the first slider at a varying speed.

10 Claims, 9 Drawing Sheets

PORTABLE BIOREACTOR

CROSS-REFERENCE TO RELATED APPLICATION

This application claims priority from Taiwanese invention patent application no. 108141778, filed on Nov. 18, 2019.

FIELD

The disclosure relates to a bioreactor, more particularly to a portable bioreactor.

BACKGROUND

A conventional bioreactor utilizes silica-coated magnetic beads for extraction of nucleic acid (DNA or RNA) from a test sample. The nucleic acid maybe further provided for use in polymerase chain reactions or other biological detections.

To improve the extraction ratio of the nucleic acid, the test sample and the magnetic beads will be repeatedly blended with reagents of different types. After procedures such as cell lysis, washing, recovery, etc., the purified and extracted nucleic acid maybe obtained from the test sample.

The above blending may be accomplished using a motor with a mixing screw, and the mixing screw for blending may be moved up and down with equal velocity. To achieve even blending, a high-priced controller with a complicated control program may be necessary. Given that the mixing screw is driven to rotate many rounds for each blending, a relatively high energy consumption may occur. In addition, such a motor with a mixing screw may not be easily carried.

As such, there is difficulty in having the conventional bioreactor used outside a lab. Furthermore, the manufacture cost of the conventional bioreactor is relatively high.

SUMMARY

Therefore, an object of the disclosure is to provide a novel portable bioreactor which may be manufactured at a reduced cost, may provide a better blending effect, and may be easily carried around.

According to the disclosure, a portable bioreactor is provided for driving displacement of at least one stirring sleeve relative to at least one tube cassette in a first direction. The portable bioreactor includes a machine frame unit and a first elevator. The machine frame unit is provided for holding the at least one tube cassette. The first elevator includes a first linear movement module, a first transmission module, and a first turning module. The first linear movement module includes a first guide rail which is mounted to the machine frame unit, and a first slider which is coupled to retain the at least one stirring sleeve, and which is slidable on the first guide rail in the first direction between a first top position, where the first slider is distal from the at least one tube cassette, and a first bottom position, where the first slider is proximate to the at least one tube cassette. The first transmission module includes a first transmission member and a first guided member. The first transmission member has a first pivotal segment and a first guiding segment which is opposite to the first pivotal segment. The first guided member is coupled slidably to the first guiding segment. One of the first guided member and the first pivotal segment is coupled to the first slider. The first turning module is coupled to the other one of the first guided member and the first pivotal segment to drive the turning of the first transmission member such that during turning of the first transmission member, the first slider, together with the at least one stirring sleeve, is moved by the first guided member to slide linearly on the first guide rail in the first direction at a varying speed.

With the provision of the portable bioreactor, the at least one stirring sleeve may be driven to move at a varying speed, which is useful for enhancing the blending effect. In addition, the portable bioreactor may be reduced in volume and manufactured at a reduced cost.

BRIEF DESCRIPTION OF THE DRAWINGS

Other features and advantages of the disclosure will become apparent in the following detailed description of the embodiment(s) with reference to the accompanying drawings, in which.

DETAILED DESCRIPTION

Figure 1:
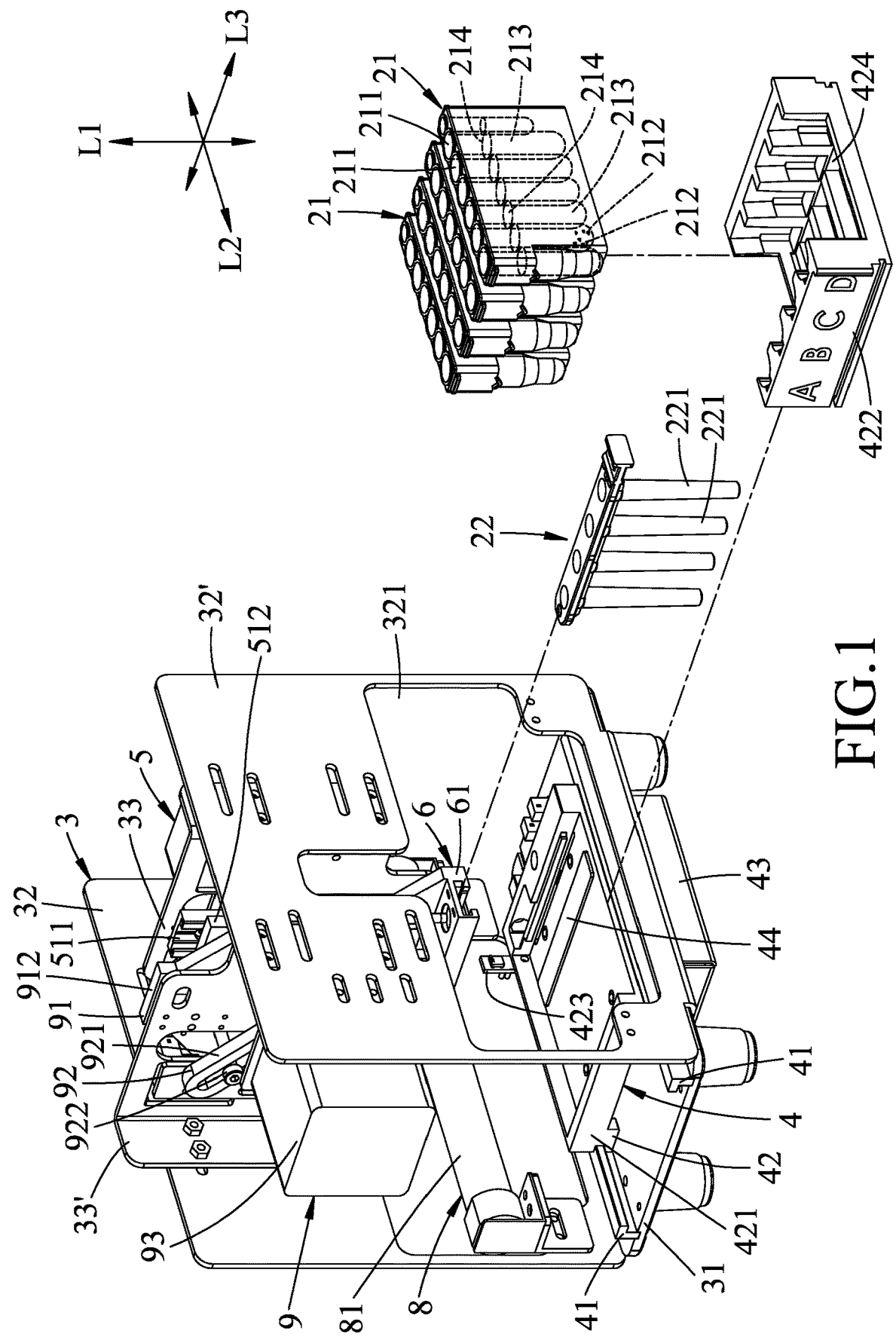
FIG. 1 is a partially exploded perspective view of a portable bioreactor according to an embodiment of the disclosure.
Figure 2:
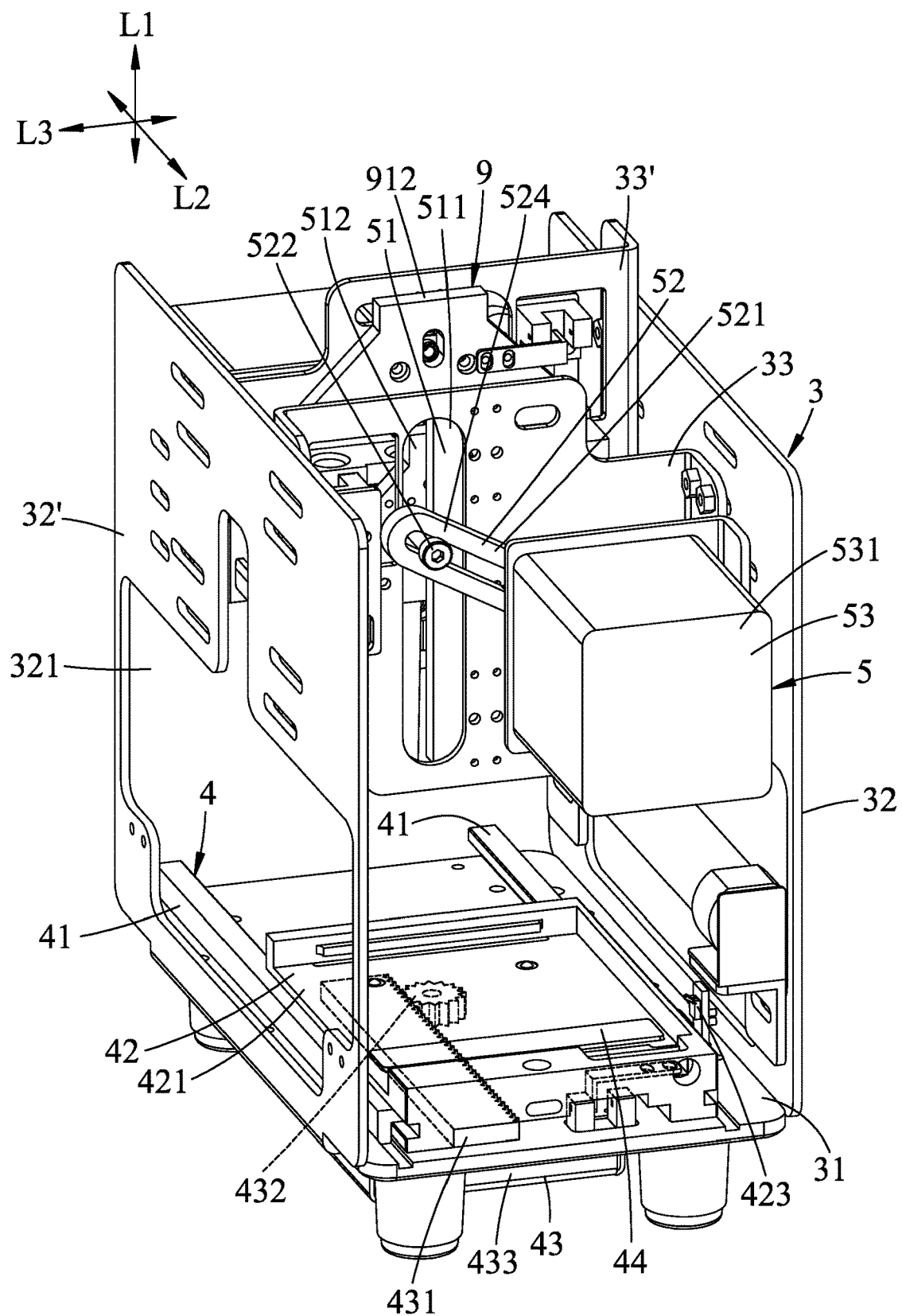
FIG. 2 is a perspective view of the portable bioreactor.
Figure 3:
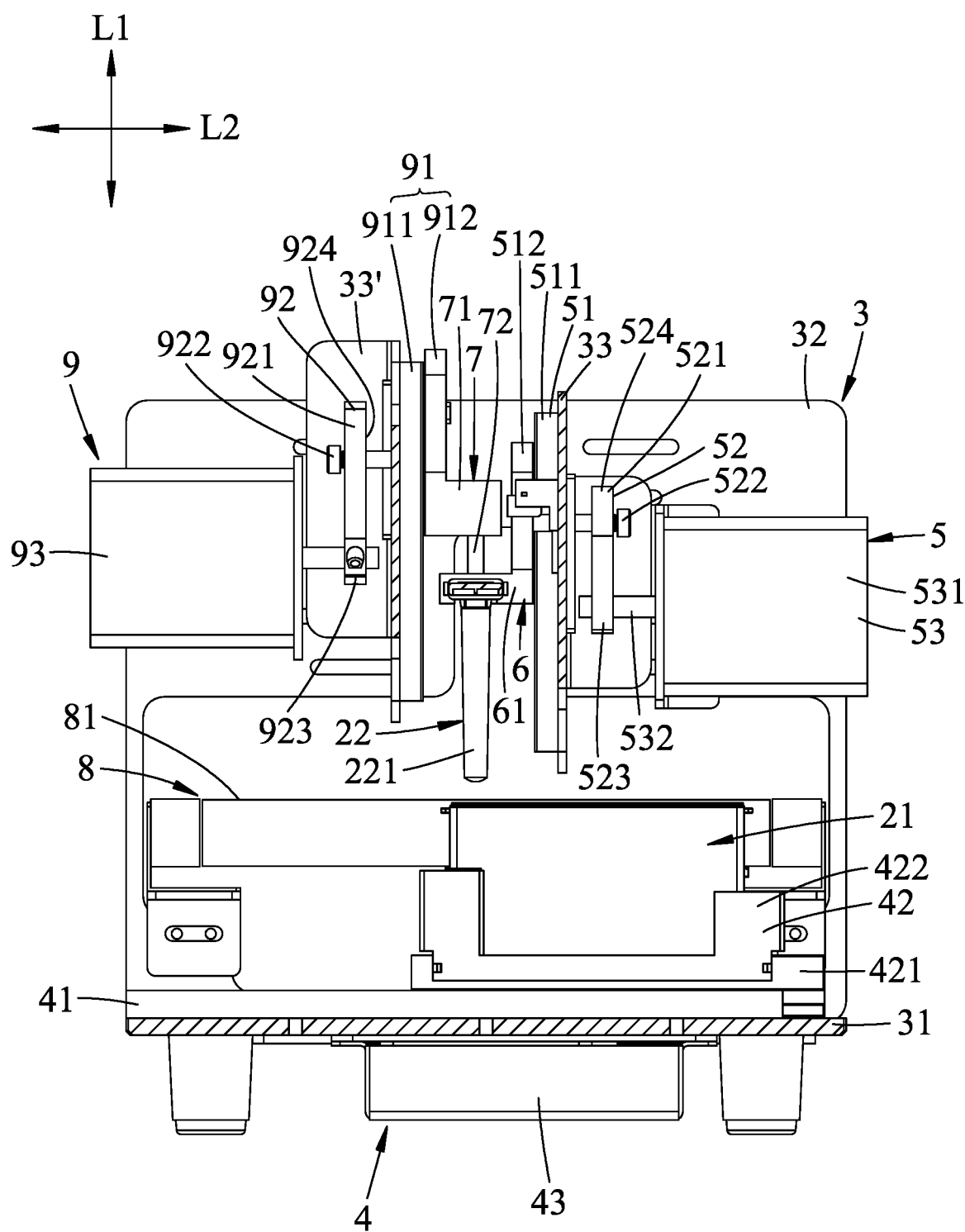
FIG. 3 is a schematic cross-sectional view of the portable bioreactor.

Referring to FIGS. 1 to 3, a portable bioreactor according to an embodiment of the disclosure, which is provided for driving displacement of at least one stirring sleeve 221 relative to at least one tube cassette 21 in a first direction (L1), is shown to include a machine frame unit 3 and a first elevator 5.

In an embodiment shown in FIG. 1, four of the tube cassettes 21 may be installed inside the portable bioreactor, and each of the tube cassettes 21 may include a plurality of tubes 211 which are displaced from each other in a second direction (L2) transverse to the first direction (L1). The tube cassettes 21 may be displaced from each other in a third direction (L3) transverse to both the first and second directions (L1, L2). Each of the tubes 211 is poured with a reagent 213 to have a liquid surface 214. One of the tubes 211 of each of the tube cassettes 21 may further have a test sample (S) and magnetic beads 212 (see FIG. 4) thereinside. Furthermore, the portable bioreactor may hold a stirring cassette 22 having four of the stirring sleeves 221 which are displaced from each other in the third direction (L3) for insertion into four corresponding tubes 211 of the four tube cassettes 21, respectively. Each of the stirring sleeves 221 may have a lower closed end and an upper open end. The magnetic beads 212 may be silica-coated.

It should be noted that the number of the tube cassettes 21 and the number of the stirring sleeves 221 in the stirring cassette 22 may be less or more than four, and may vary based on requirements. In addition, the tube cassettes 21 may be replaced with a block with an array of elongated holes each being poured with the above-mentioned mixture.

The machine frame unit 3 is provided for holding the tube cassette(s) 21. In an embodiment shown in FIGS. 1 to 3, the machine frame unit 3 may include a base frame 31, a first side frame 32, a second side frame 32', a first bracket 33, and a second bracket 33'. The first and second side frames 32, 32' are disposed on the base frame 31 to be spaced apart from each other in the third direction (L3). Each of the first and second side frames 32, 32' may have an opening 321. In another embodiment, the opening 321 may be formed in only one of the first and second side frames 32, 32'. Each of the first and second brackets 33, 33' may extend in the third direction (L3) to interconnect the first and second side frames 32, 32', and the first and second brackets 33, 33' may be spaced apart from each other in the second direction (L2).

Although the first and second side frames 32, 32' are provided in the embodiment shown in FIG. 1, the machine frame unit 3 in another embodiment may include only one of the first and second side frames 32, 32' and the first and second brackets 33, 33' may be mounted on the one of the first and second side frames 32, 32'. In a modified embodiment, the first and second side frames 32, 32' may extend in the second direction (L2) to span across two opposite sides of the base frame 31. In an embodiment shown in FIGS. 1 to 3, the portable bioreactor may further include a carrying unit 4 which may be mounted on the base frame 31 of the machine frame unit 3 and which may include two base rails 41, a carrier member 42, and a drive module 43.

Each of the base rails 41 extends in the second direction (L2), and the base rails 41 are mounted on the base frame 31 to be spaced apart from each other in the third direction (L3).

The carrier member 42 is coupled slidably on the base rails 41 and is configured for carrying the tube cassette(s) 21. In an embodiment shown in FIG. 1, the carrier member 42 may include a base portion 421 and a carrier portion 422. The base portion 421 is slidably coupled on the base rails 41. The carrier portion 422 is configured for carrying the tube cassette(s) 21, and is detachably mounted on the base portion 421 so as to permit removal of the carrier portion 421, together with the tube cassette(s) 21, from the machine frame unit 3 via the opening 321 of one of the first and second side frames 32, 32'. Alternatively, the first and second side frames 32, 32' may not have the opening 321, and the carrier portion 421 may be moved in the second direction (L2) for installation or detachment.

In addition, a sensor 423 maybe mounted on the base portion 421 for detecting whether or not the carrier portion 422 is precisely mounted on the base portion 421. The drive module 43 may be coupled to drive the sliding of the carrier member 42 relative to the machine frame unit 3. In an embodiment shown in FIG. 2, the drive module 43 may include a rack piece 431, a drive gear 432, and a drive member 433. The rack piece 431 is mounted beneath the carrier member 42. The drive gear 432 is mounted on the base frame 31 of the machine frame unit 3, and is configured to mesh with the rack piece 431. The drive member 433 is coupled to drive rotation of the drive gear 432 so as to drive the sliding of the carrier member 42 on the base rails 41. It should be noted that, in the other embodiment, the sliding of the carrier member 42 may be belt-driven.

In an embodiment shown in FIGS. 1 and 2, the carrying unit 4 may further include a heating member 44 which is mounted on the base portion 421, and the carrier portion 422 may have at least one through hole 424 in a position corresponding to the heating member 44 so as to permit the tubes 211 above the heating member 44 to be heated for facilitating extraction of the test samples (S) in the corresponding tubes 211. In an embodiment, the heating member 44 may include, but not limited to, a heating metal plate.

The first elevator 5 is mounted to the machine frame unit 3 and includes a first linear movement module 51, a first transmission module 52, and a first turning module 53.

Figure 4:
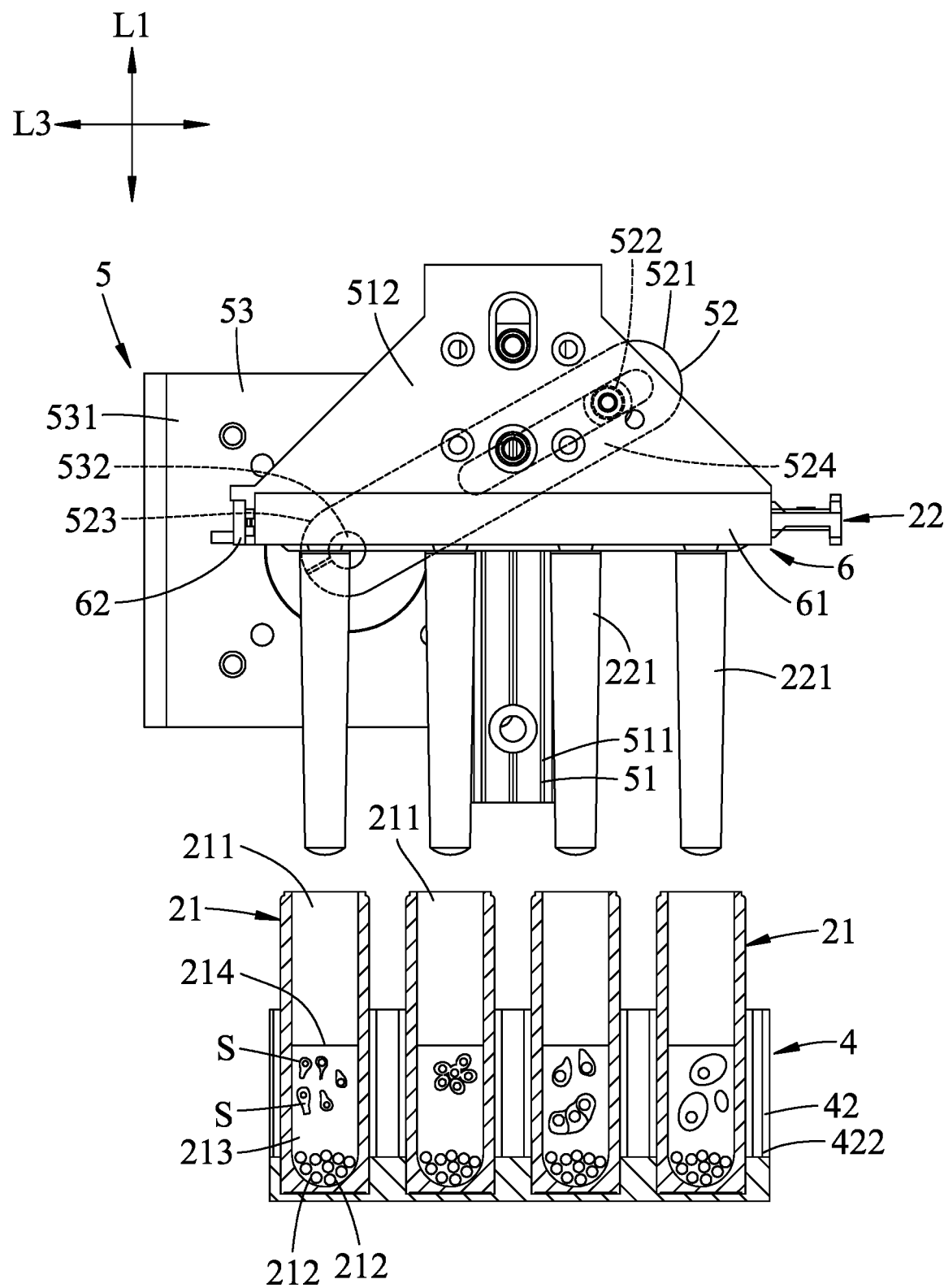
FIG. 4 is a fragmentary, partially cross-sectional view illustrating a first slider of the portable bioreactor in a first top position.
Figure 5:
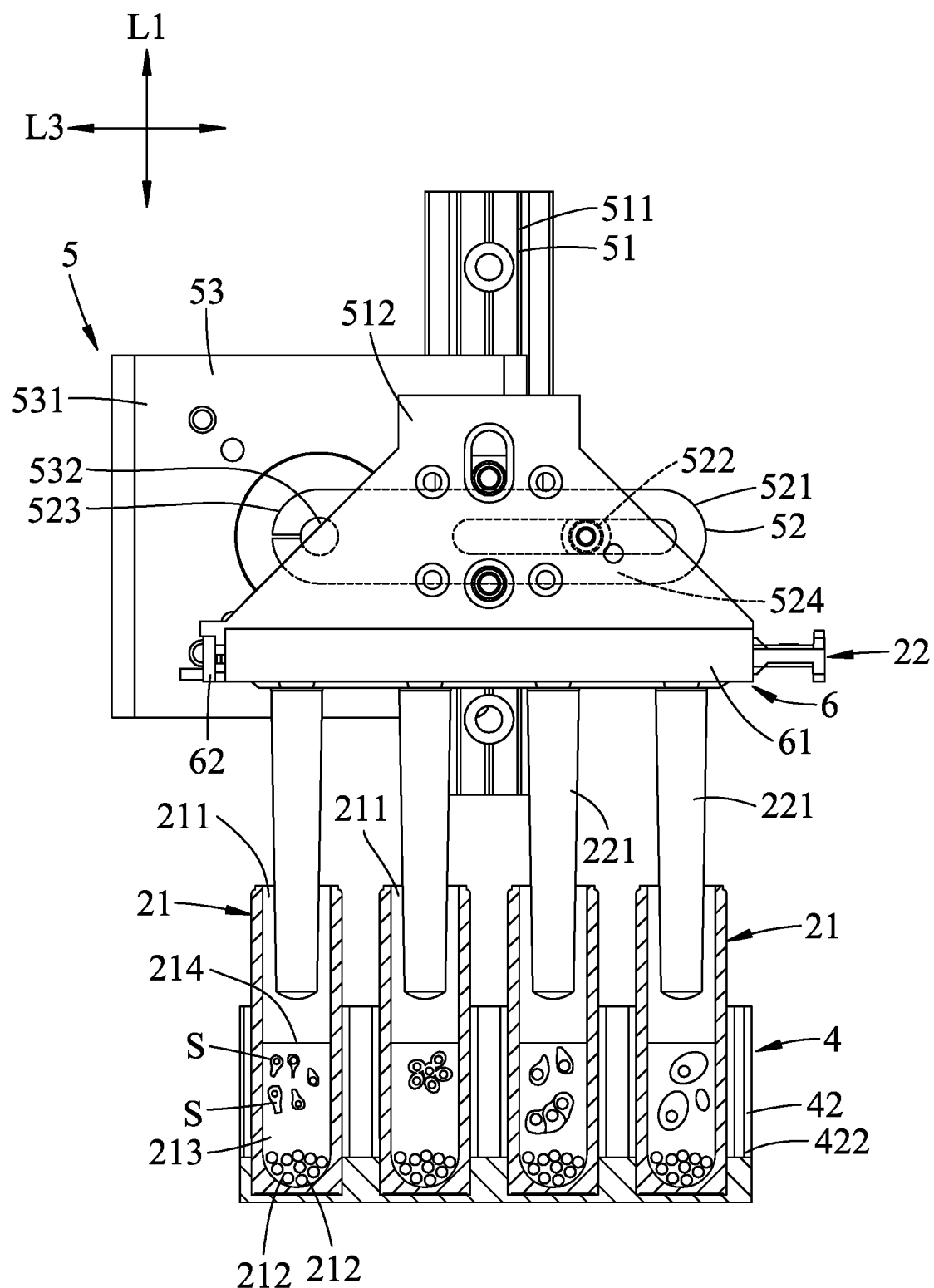
FIG. 5 is similar to FIG. 4 but illustrating the first slider in a middle position.
Figure 6:
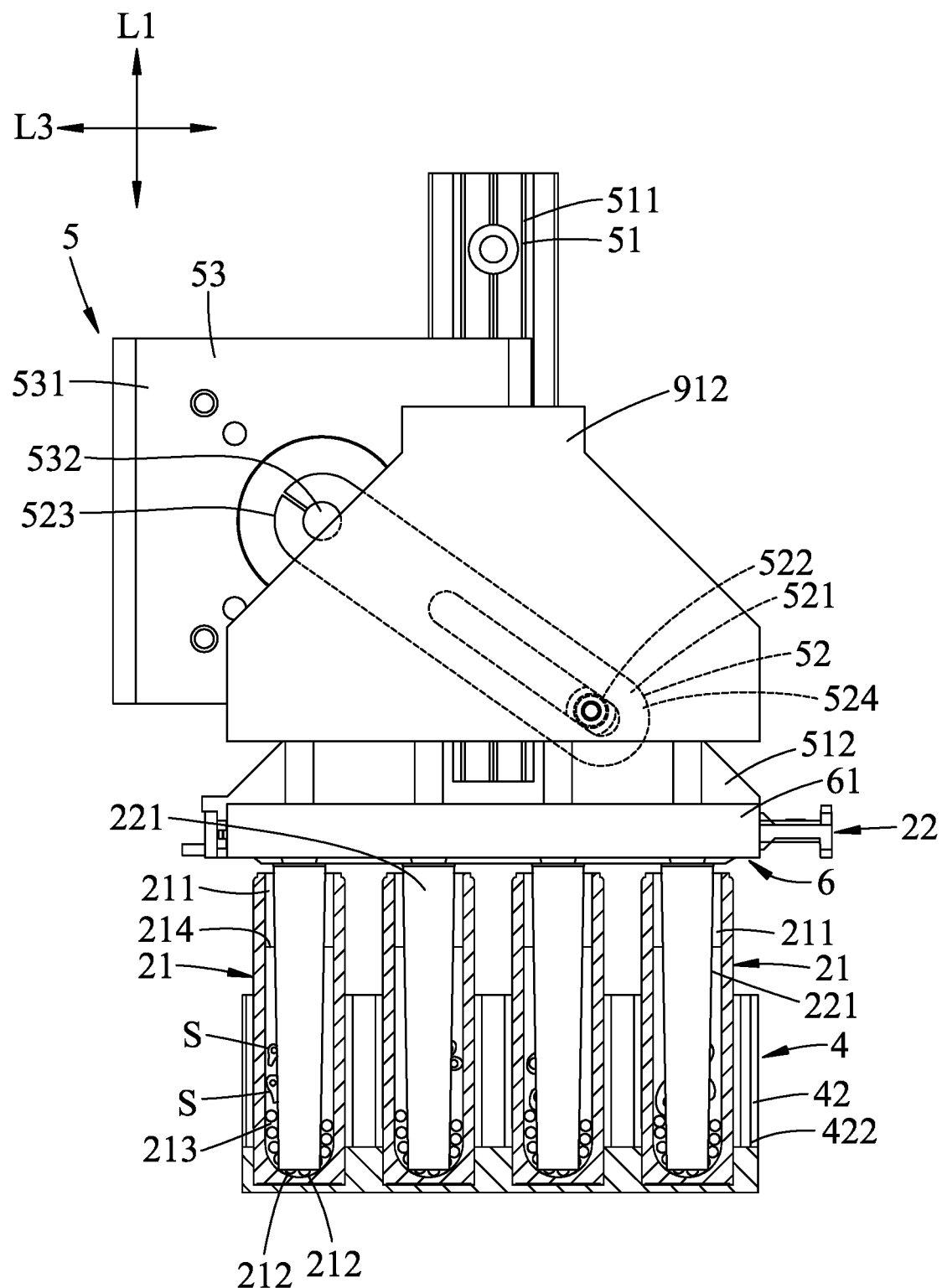
FIG. 6 is similar to FIG. 4 but illustrating the first slider in a first bottom position and further illustrating a second slider in a second bottom position.
Figure 9:
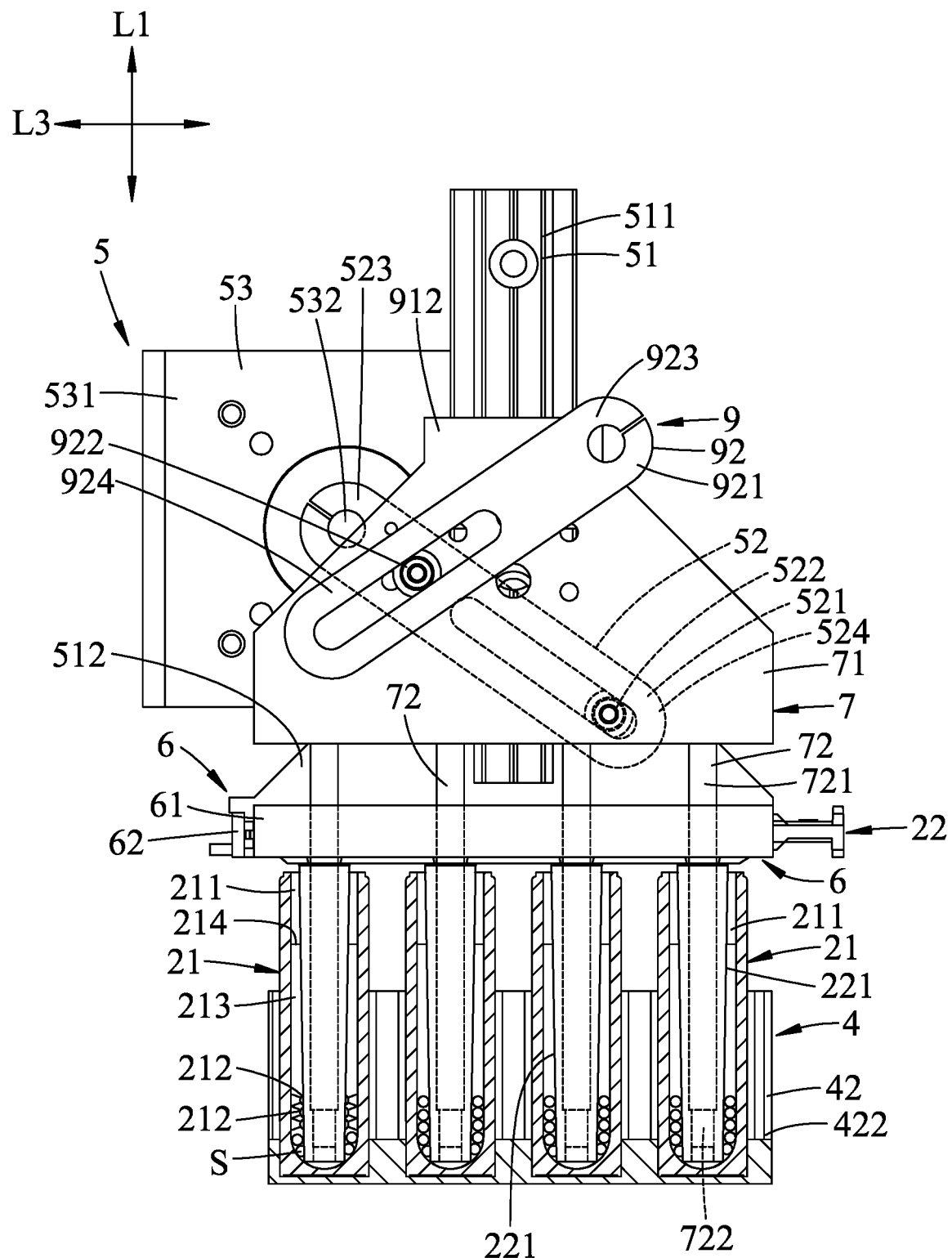
FIG. 9 is similar to FIG. 6 but further illustrating a second transmission module coupled on the second slider, and elongated rods inside a tube cassette.

The first linear movement module 51 includes a first guide rail 511 and a first slider 512. The first guide rail 511 may be mounted on the first bracket 33. The first slider 512 is coupled to retain the stirring cassette 22, and is slidable on the first guide rail 511 in the first direction (L1) between a first top position and a first bottom position. In the first top position, as shown in FIG. 4, the first slider 512 is distal from the tube cassette(s) 21. In the first bottom position, as shown in FIGS. 6 and 9, the first slider 512 is proximate to the tube cassette(s) 21. The first slider 512 is slidable to a middle position (FIG. 5) between first top and bottom positions so as to permit bottoms of the stirring sleeves 221 to be disposed above and proximate to the liquid surfaces 214 of the corresponding tubes 211 of the tube cassettes 21.

The first transmission module 52 includes a first transmission member 521 having a first pivotal segment 523 and a first guiding segment 524 which is opposite to the first pivotal segment 523. The first guided member 522 is coupled slidably to the first guiding segment 524. One of the first guided member 522 and the first pivotal segment 523 is coupled to the first slider 512.

The first turning module 53 is coupled to the other one of the first guided member 522 and the first pivotal segment 523 to drive the turning of the first transmission member 52 such that during turning of the first transmission member 52, the first slider 512, together with the stirring sleeve(s) 221, is moved by the first guided member 522 to slide linearly on the first guide rail 511 in the first direction (L1) at a varying speed.

In an embodiment shown in FIGS. 3 to 6, the first guided member 522 is coupled to the first slider 512, and the first turning module 53 is coupled to the first pivotal segment 523.

In an embodiment shown in FIGS. 3 to 6, the first turning module 53 may include a drive body 531 and an output shaft 532 which extends along a shaft axis in the second direction (L2), and which is actuated by the drive body 531 to be turnable about the shaft axis. The drive body 531 may be mounted to the first side frame 32, and the output shaft 532 is capable of turning in both clockwise and counterclockwise directions and is coupled to the first pivotal segment 523.

In an embodiment shown in FIGS. 2 and 4 to 6, the first guiding segment 524 has an elongated slot configured to permit the first guided member 522 to be slidably engaged therein.

When the output shaft 532 is actuated by the drive body 531 to turn, the turning of the output shaft 532 is permitted to be translated by the first transmission module 52 into linear sliding of the first slider 512 in the first direction (L1) at a varying speed. In the meanwhile, the stirring cassette 22 is also driven to move at a varying speed.

In an embodiment shown in FIGS. 3 to 6, the first turning module 53 and the first guided member 522 are disposed at two opposite sides of the first guide rail 511 in the third direction (L3). In addition, the first turning module 53 is a stepper motor which is low in cost and may precisely transmit a relatively high torque to the first transmission module 52. In this connection, the stirring cassette 22 may be stably displaced at a varying speed.

Figure 7:
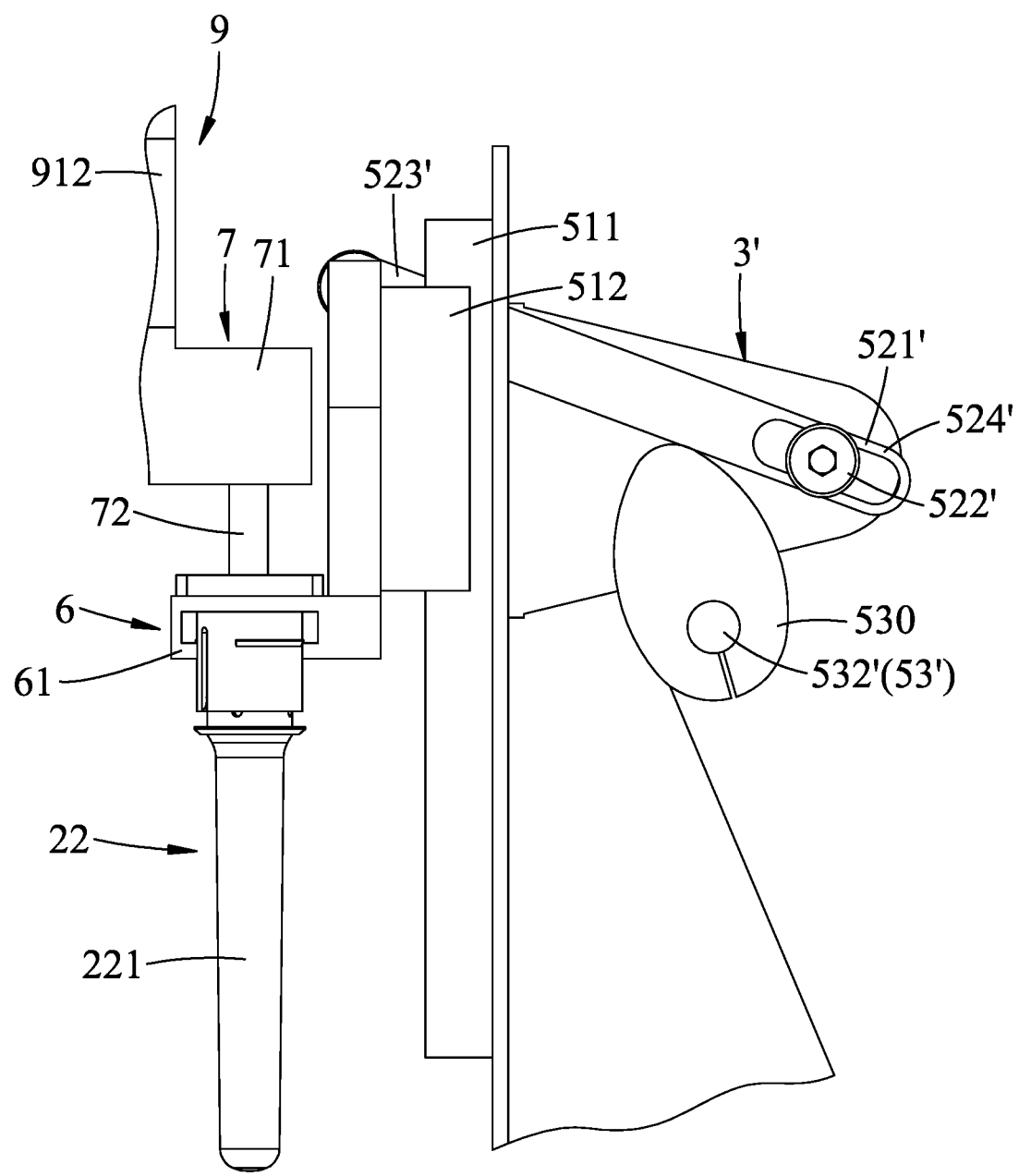
FIG. 7 is a fragmentary schematic view illustrating a modified embodiment of the portable bioreactor.

As shown in FIG. 7, in a modified embodiment of the portable bioreactor, the first pivotal segment 523' of the first transmission member 521' is coupled to the first slider 512, and the output shaft 532' of the first turning module 53' has a cam member 530 which is mounted on the output shaft 532', and which is coupled to the first guided member 522' through the first guiding segment 524' of the first transmission member 521'. The first guided member 522' may be mounted to the machine frame unit 3' and may be slidably engaged in the elongated slot of the first guiding segment 524' of the first transmission member 521'.

Figure 8:
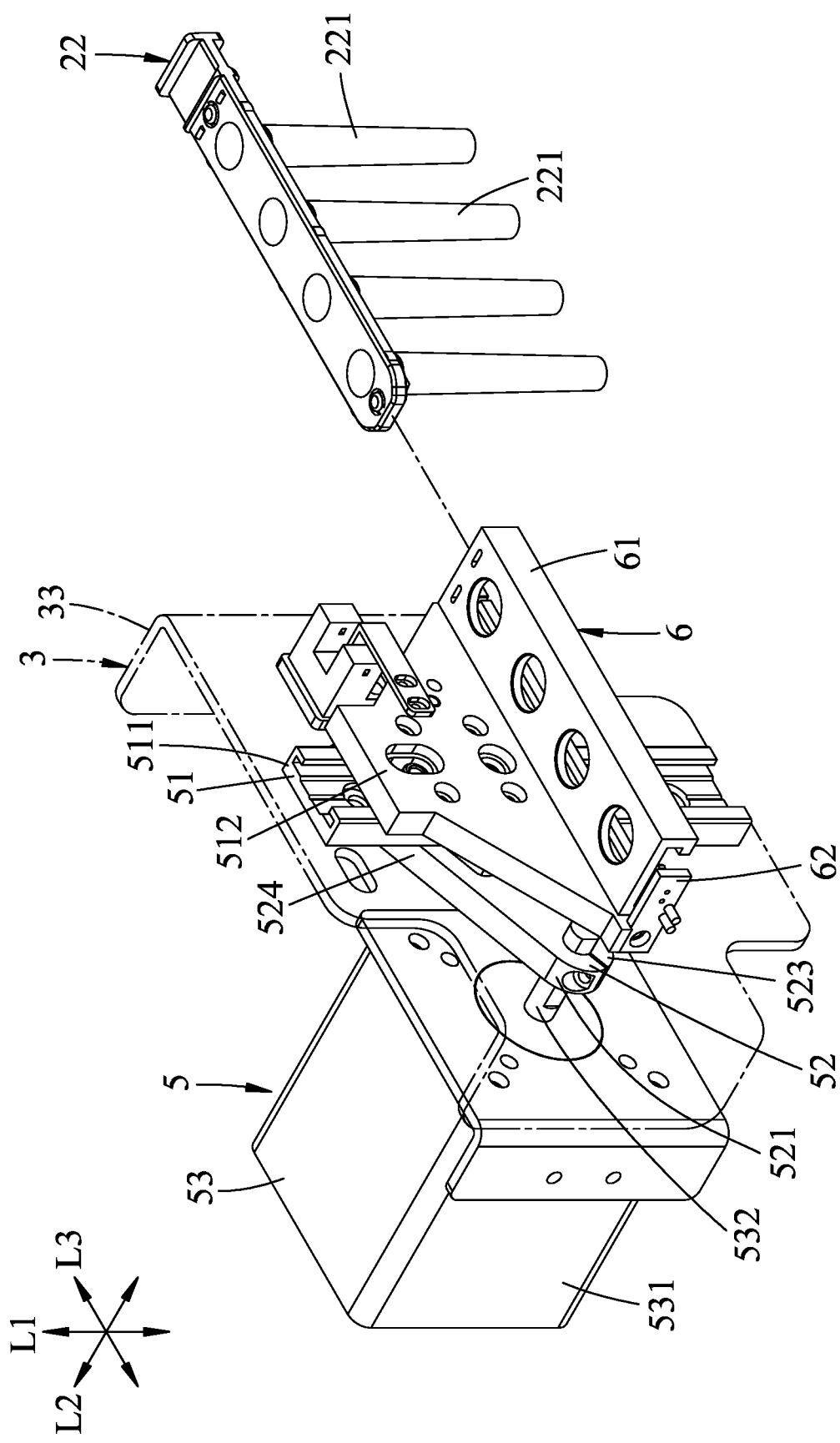
FIG. 8 is a fragmentary, partially exploded perspective view illustrating how a stirring cassette is mounted to the first slider through a cassette holder.

As shown in FIGS. 1, 3, and 8, a cassette holder 6 is mounted to the first slider 512 and may include a holder body 61 configured for holding the stirring cassette 22 and a sensor 62. The stirring cassette 22 may be installed to the holder body 61 via the opening 321 of one of the first and second side frames 32, 32'. The sensor 62 is provided for detecting whether or not the stirring cassette 22 is securely held by the holder body 61.

It should be noted that, in a modified embodiment, the stirring sleeves 221 maybe individually mounted to the holder body 61. For example, the stirring sleeves 221 may be previously disposed in the tubes 211 of one of the tube cassettes 21. When the first slider 512 is moved in the first direction (L1) to the first bottom position (FIG. 6), the stirring sleeves 221 may be connected to the holder body 61.

In an embodiment shown in FIGS. 1, 3, and 9, the portable bioreactor may further include a transfer unit 7 and a second elevator 9.

The transfer unit 7 may include a mount body 71 and four elongated rods 72 which are retained by the mount body 71 and which are configured to insert into the stirring sleeves 221, respectively. Each of the elongated rods 72 has a rod body 721 connected to the mount body 71, and a bottom magnetic attractive portion 722.

The second elevator 9 is mounted to the machine frame unit 3 and is spaced apart from the first elevator 5 in the second direction (L2). The second elevator 9 includes a second linear movement module 91, a second transmission module 92, and a second turning module 93.

The second linear movement module 91 may include a second guide rail 911 and a second slider 912. The second guide rail 911 maybe mounted on the second bracket 33'. The second slider 912 is coupled to retain the transfer unit 7 to permit the elongated rods 72 to be inserted into the stirring sleeves 221, respectively. The second slider 912 is slidable on the second guide rail 911 in the first direction (L1) between a second top position (FIG. 3) and a second bottom. position (FIG. 9) relative to the tube cassette(s) 21. In an embodiment shown in FIGS. 3 and 9, the mount body 71 and the second slider 912 are integrally formed. In other embodiments, the mount body 71 and the second slider 912 may be separately formed and connected to each other.

The second transmission module 92 includes a second transmission member 921 and a second guided member 922. The second transmission member 921 has a second pivotal segment 923 and a second guiding segment 924 which is opposite to the second pivotal segment 923. The second guided member 922 is coupled slidably to the second guiding segment 924. One of the second guided member 922 and the second pivotal segment 923 is coupled to the second slider 912. The second transmission module 92 may have the same structure as that of the first transmission module 52.

The second turning module 93 is mounted on the second side frame 32' and is coupled to the other one of the second guided member 922 and the second pivotal segment 923 to drive the turning of the second transmission member 921 such that when the first slider is in the first bottom position (FIGS. 6 and 9), during turning of the second transmission member 921, the second slider 912, together with the transfer unit 7, is permitted to be moved by the second guided member 922 to slide linearly to the second bottom position at a varying speed, thereby allowing magnetic beads 212 inside the corresponding tubes 211 of the tube cassettes 21 to be attracted around the stirring sleeves 221, respectively. The second turning module 93 may have the same structure as that of the first turning module 53.

In an embodiment shown in FIGS. 3 and 9, the second guided member 922 is coupled to the second slider 912, and the second turning module 93 is coupled to the second pivotal segment 923. The second guiding segment 924 has an elongated slot configured to permit the second guided member 922 to be slidably engaged therein.

In an embodiment shown in FIGS. 1 and 3, the portable bioreactor may further include a sterilization unit 8 which may be mounted to one of the first and second side frames 32, 32', and which may include an UV light 81 in proximity to the carrying unit 4 and the transfer unit 7.

In the following paragraphs, the procedures for extracting nucleic acid using the portable bioreactor are described.

In Step 1, a plurality of tube cassettes 21 and a stirring cassette 22, which have not been used, are prepared. Each of the tube cassettes 21 has a first tube 211, a second tube 211, a third tube 211, and so on, which are displaced from each other in the second direction (L1). The test samples (S) and the magnetic beads 212 are disposed in the first tubes 211 of the tube cassettes 21, respectively. The first tubes 211, the second tubes 211, the third tubes 211 and so on of the tube cassettes 21 are poured with different reagents 213.

In Step 2, the first slider 512 is lowered to permit the stirring cassette 22 to be mounted to the holder body 61 of the cassette holder 6. Then, the first slider 512 is elevated to move away from the base frame 31. In this moment, the carrier portion 422, which carries the tube cassettes 21 thereon, is permitted to be mounted on the base portion 421. For safe extraction, it is necessary to check whether or not the carrier portion 422 and the stirring cassette 22 are securely mounted according to the signals from the sensors 423, 62.

From Steps 3 to 6, how the test samples (S) are subject to procedures of cell lysis, washing, and recovery is further described.

In Step 3, each of the test samples (S) in the corresponding first tube 211 is mixed with magnetic beads 212 in a cell lysis reagent 213 for extracting nucleic acid. In this embodiment, the stirring sleeves 221 are driven by the first elevator 5 to move up and down at a varying speed so as to homogenize the mixture and to reduce the time required for cell lysis. In this step, the second slider 912 is kept in the second top position so as to keep the transfer unit 7 at the top side.

In addition, it should be noted that the portable bioreactor of the disclosure may have the following effects. When the first slider 512 is moved to the middle position (FIG. 5), the bottom of each of the stirring sleeves 221 is disposed above and proximate to the liquid surface 214 of the corresponding tube 211. A distance between the first guided member 522 and the output shaft 532 when the first slider 512 in the middle position is shorter than a distance between the first guided member 522 and the output shaft 532 when the first slider 512 in the first top or bottom position (FIG. 4 or 6). It means that an instantaneous velocity of the first slider 512 when moving to the middle position is slower than an instantaneous velocity of the first slider 512 when moving toward the first top or bottom position. As such, when each of the stirring sleeves 221 is moved through the corresponding liquid surface 214, the mixture inside the corresponding tube 211 may be prevented from spraying out. In other embodiments, the distance between the first guided member 522 and the output shaft 532 in the first direction (L1) may be variable to thereby change the instantaneous velocities of the first slider 512 at different positions.

In Step 4, the homogenized mixture including the extracted nucleic acid may adhere to the magnetic beads 212, and the second slider 912 is moved downwardly to the second bottom position (FIG. 9) to bring the elongated rods 72 to be respectively inserted into the stirring sleeves 221 in the first tubes 211 so as to permit the magnetic beads 212 together with the homogenized mixture in the first tubes 211 to be attracted around the stirring sleeves 221, respectively. Thereafter, the first slider 512 and the second slider 912 are simultaneously and respectively driven to the first top position and the second top position to permit the magnetic beads 212 together with the homogenized mixture to move away from the first tubes 211, respectively. It should be noted that the second elevator 9 for driving movement of the transfer unit 7 may be replaced by other devices which is driven by belt(s), screw(s), or the other linkage mechanism(s).

In Step 5, the carrier member 42 is driven to move in the second direction (L2) to permit the stirring sleeves 221 to be disposed above the second tubes 211 of the tube cassettes 21, respectively. The second tubes 211 are poured with different reagents 213 from those in the first tubes 211 to remove impurities from the nucleic acid. Then, the first slider 512 is moved up and down like Step 3, and the magnetic beads 212 are removed from the second tubes 211 like Step 4 and are transferred to the third tubes 211 of the tube cassettes 21 like Step 5. Those steps are repeated several times for washing and purifying the nucleic acid. In addition, the heating member 44 may be used for heating the corresponding tubes 211 to accelerate the extraction.

In Step 6, the magnetic beads 212 are transferred to the last tubes 211 of the tube cassettes 211. The last tubes 211 are poured with reagents 213 for detaching and recovering the extracted nucleic acid from the magnetic beads. If necessary, the first slider 512 may be moved up and down like Step 3. Thereafter, the magnetic beads 212 are removed from the last tubes 211 like Step 4, and the extracted nucleic acid is left in the last tubes 211.

In step 7, after removal of the stirring cassette 22 from the first elevator 5, the sterilization unit 8 is turned on for sterilization of the carrying unit and the transfer unit 7.

The following tests were conducted based on the above steps using the portable bioreactor of the disclosure and the conventional device (a motor with a mixing screw) described in the background section. The results were summarized in the following Tables 1 and 2. Those tests were conducted by using the same steps and the same reagents except for using different devices. Two test samples were prepared, one of which was 200 μl human blood, and the other of which was 40 mg tissue from the chicken spleen. Each of the test samples for each device was extracted for two times. The concentration of the extracted nucleic acid in each test was measured using a spectrophotometer. When the OD260/OD280 ratio for the extracted nucleic acid was greater than 1.6, it means that the extraction was sufficient. It should be noted that in the following Tables, the recovery ratio of the extracted nucleic acid using the portable bioreactor of the disclosure was calculated based on having the recovery ratio of the extracted nucleic acid by using the conventional device to be 100%.

TABLE 1

Extraction using 200 μl human blood

|  | Test | Concentration of nucleic acid (ng/μl) | OD260/OD280 ratio | Avg. Concentration (ng/μl) | Recovery ratio |
|---|---|---|---|---|---|
| Conventional device | 1 | 18.2 | 1.86 | 17.05 | 100% |
|  | 2 | 15.9 | 1.88 |  |  |
| Portable bioreactor | 1 | 25.8 | 1.97 | 24.65 | 145% |
|  | 2 | 23.5 | 1.83 |  |  |

TABLE 2

Extraction using 40 mg chicken spleen

|  | Test | Concentration of nucleic acid (ng/μl) | OD260/OD280 ratio | Avg. Concentration (ng/μl) | Recovery ratio |
|---|---|---|---|---|---|
| Conventional device | 1 | 58.7 | 1.95 | 54.5 | 100% |
|  | 2 | 50.3 | 1.94 |  |  |
| Portable bioreactor | 1 | 63.6 | 1.9 | 62.95 | 116% |
|  | 2 | 62.3 | 1.95 |  |  |

Based on the above, the portable bioreactor of the disclosure has the following advantages:

1) Because the first slider 512, during cell lysis of the test samples (S) in the cell lysis reagent 213, may be moved up and down at a varying speed, the test samples (S) inside the first tubes 211 maybe mixed with the magnetic beads 212 in a more efficient way. Therefore, the recovery ratio of the nucleic acid was relatively high when using the portable bioreactor of the disclosure.

2) Because the first slider 512, during washing and purifying of the extracted nucleic acid, may be moved up and down at a varying speed, the turbulence intensity of the homogenized mixture inside the second or the following tubes may increase and in turn, lead to better blending and shortened blending time.

3) With the provision of the first or second transmission module 52, 92, the portable bioreactor may be reduced in size and weight, and the program for controlling the first or second turning module 53, 93 may be simplified. Thus, the portable bioreactor of the disclosure may be easily carried and manufactured at a lower cost.

4) Because the output shaft 532 of the first or second turning module 53, 93 may be turned in a relatively low degree for driving the first or second transmission module 52, 92, the portable bioreactor of the disclosure may be battery-driven and may have lower energy consumption in comparison with the conventional device. Thus, the portable bioreactor is convenient for carrying around and extracting nucleic acid outside a lab.

In the description above, for the purposes of explanation, numerous specific details have been set forth in order to provide a thorough understanding of the embodiment(s). It will be apparent, however, to one skilled in the art, that one or more other embodiments may be practiced without some of these specific details. It should also be appreciated that reference throughout this specification to "one embodiment," "an embodiment," an embodiment with an indication of an ordinal number and so forth means that a particular feature, structure, or characteristic may be included in the practice of the disclosure. It should be further appreciated that in the description, various features are sometimes grouped together in a single embodiment, figure, or description thereof for the purpose of streamlining the disclosure and aiding in the understanding of various inventive aspects, and that one or more features or specific details from one embodiment may be practiced together with one or more features or specific details from another embodiment, where appropriate, in the practice of the disclosure.

While the disclosure has been described in connection with what is (are) considered the exemplary embodiment(s), it is understood that this disclosure is not limited to the disclosed embodiment(s) but is intended to cover various arrangements included within the spirit and scope of the broadest interpretation so as to encompass all such modifications and equivalent arrangements.

What is claimed is:

1. A portable bioreactor for driving displacement of at least one stirring sleeve relative to at least one tube cassette in a first direction, said portable bioreactor comprising:
   a machine frame unit for holding the at least one tube cassette; and
   a first elevator including
      a first linear movement module including a first guide rail which is mounted to said machine frame unit, and a first slider which is coupled to retain the at least one stirring sleeve, and which is slidable on said first guide rail in the first direction between a first top position, where said first slider is distal from the at least one tube cassette, and a first bottom position, where said first slider is proximate to the at least one tube cassette,
      a first transmission module including
         a first transmission member having a first pivotal segment and a first guiding segment which is opposite to said first pivotal segment, and
         a first guided member coupled slidably to said first guiding segment, one of said first guided member and said first pivotal segment being coupled to said first slider, and
      a first turning module which is coupled to the other one of said first guided member and said first pivotal segment to drive the turning of said first transmission member such that during turning of said first transmission member, said first slider, together with the at least one stirring sleeve, is moved by said first guided member to slide linearly at a varying speed on said first guide rail in the first direction.

2. The portable bioreactor according to claim 1, wherein said first slider is slidable to a middle position which is between the first top and bottom positions so as to permit a bottom of the at least one stirring sleeve to be disposed above and proximate to a liquid surface inside the at least one tube cassette; and
   wherein during sliding of said first slider, an instantaneous velocity of said first slider when moving to the middle position is slower than an instantaneous velocity of said first slider when moving toward the first top position.

3. The portable bioreactor according to claim 1, wherein said first turning module includes a drive body and an output shaft which extends along a shaft axis in a second direction transverse to the first direction, and which is actuated by said drive body to be turnable about the shaft axis; and
   wherein said first turning module and said first guided member are disposed at two opposite sides of said first guide rail in a third direction which is transverse to both the first and second directions.

4. The portable bioreactor according to claim 1, wherein said first guided member is coupled to said first slider, and said first turning module is coupled to said first pivotal segment.

5. The portable bioreactor according to claim 1, wherein said first guiding segment has an elongated slot configured to permit said first guided member to be slidably engaged therein.

6. The portable bioreactor according to claim 1, further comprising a carrying unit which includes
   two base rails each extending in a second direction transverse to the first direction, said base rails being mounted on said machine frame unit to be spaced apart from each other in a third direction transverse to both the first and second directions,
   a carrier member which is coupled slidably on said base rails and which is configured for carrying the at least one tube cassette, and
   a drive module coupled to drive the sliding of said carrier member relative to said machine frame unit.

7. The portable bioreactor according to claim 6, wherein said drive module includes
   a rack piece mounted beneath said carrier member,
   a drive gear mounted on said machine frame unit, and configured to mesh with said rack piece, and
   a drive member coupled to drive rotation of said drive gear so as to drive the sliding of said carrier member on said base rails.

8. The portable bioreactor according to claim 6,
   wherein said machine frame unit includes a base frame and a side frame which is disposed on said base frame, and which has an opening;
   wherein said base rails are mounted on said base frame; and
   wherein said carrier member includes a base portion which is slidably coupled on said base rails, and a carrier portion which is configured for carrying the at least one tube cassette, and which is detachably mounted on said base portion so as to permit removal of said carrier portion, together with the at least one tube cassette, from the machine frame unit via said opening.

9. The portable bioreactor according to claim 6,
   wherein said carrying unit further includes a heating member; and
   wherein said carrier member includes
      a base portion which is slidably coupled on said base rails, and which has said heating member mounted thereon, and
      a carrier portion which is detachably mounted on said base portion for carrying the at least one tube cassette, and which has a through hole in a position corresponding to said heating member.

10. The portable bioreactor according to claim 1, further comprising:
   a transfer unit including at least one elongated rod which is configured to insert into the at least one stirring sleeve, and which has a bottom magnetic attractive portion; and
   a second elevator which is mounted to said machine frame unit, and which is spaced apart from said first elevator in a second direction transverse to the first direction, said second elevator including
      a second linear movement module including a second guide rail, and a second slider which is coupled to retain said transfer unit to permit said elongated rod to be inserted into the at least one stirring sleeve, said second slider being slidable on said second guide rail in the first direction between a second top position and a second bottom position relative to the at least one tube cassette, a second transmission module including
- a second transmission member having a second pivotal segment and a second guiding segment which is opposite to said second pivotal segment, and
- a second guided member coupled slidably to said second guiding segment, one of said second guided member and said second pivotal segment being coupled to said second slider, and a second turning module which is coupled to the other one of said second guided member and said second pivotal segment to drive the turning of said second transmission member such that when said first slider is in the first bottom position, during turning of said second transmission member, said second slider, together with said transfer unit, is permitted to be moved by said second guided member to slide linearly to the second bottom position at a varying speed, thereby allowing magnetic beads inside the at least one tube cassette to be attracted around the at least one stirring sleeve.

\* \* \* \* \*